United States Patent
Roe

(10) Patent No.: US 9,445,756 B2
(45) Date of Patent: *Sep. 20, 2016

(54) DYNAMIC INTEGRATED LANCING TEST STRIP WITH STERILITY COVER

(75) Inventor: Steven N. Roe, San Mateo, CA (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 1010 days.

This patent is subject to a terminal disclaimer.

(21) Appl. No.: 12/887,612

(22) Filed: Sep. 22, 2010

(65) Prior Publication Data

US 2011/0009775 A1    Jan. 13, 2011

Related U.S. Application Data

(63) Continuation of application No. 11/070,502, filed on Mar. 2, 2005, now Pat. No. 7,815,579.

(51) Int. Cl.
*A61B 5/00*   (2006.01)
*B65D 81/00*  (2006.01)
(Continued)

(52) U.S. Cl.
CPC ..... *A61B 5/14532* (2013.01); *A61B 5/150274* (2013.01); *A61B 5/150282* (2013.01); *A61B 5/150297* (2013.01); *A61B 5/157* (2013.01); *A61B 5/150312* (2013.01)

(58) Field of Classification Search
CPC ............ A61B 5/1411; A61B 5/15186; A61B 5/14532
USPC ................. 600/583, 584, 576; 422/22, 40; 606/181, 183
See application file for complete search history.

(56) References Cited

U.S. PATENT DOCUMENTS 3,640,267 A   2/1972   Hurtig et al.
3,640,388 A   2/1972   Ferrari
(Continued)

FOREIGN PATENT DOCUMENTS

DE   28 03 345 B1   6/1979
DE   35 15 420 A1   10/1986
(Continued)

OTHER PUBLICATIONS

U.S. Appl. No. 11/537,791, Oct. 2, 2006, Calasso et al.
(Continued)

*Primary Examiner* — Max Hindenburg
*Assistant Examiner* — Jonathan M Foreman
(74) *Attorney, Agent, or Firm* — Woodard, Emhardt, Moriarty, McNett & Henry LLP

(57) ABSTRACT

An integrated lancing test strip includes a test strip and a lancet packet coupled to the test strip. The lancet packet includes a sterility sheet enclosing a lancet to maintain the sterility of the lancet and prevent cross-contamination between the test strip and the lancet. The sterility sheet allows the lancet to be sterilized separately from the test strip. The sterility sheet gives the integrated strip a low profile, which is attractive for packaging multiple integrated strips in cassettes, drums, magazines or the like. In one form, the integrated strip is loaded in a meter that includes an adjustment mechanism that adjusts the position of the test strip relative to the skin being sampled. This allows the user to adjust the position of the test strip so as to not apply excessive pressure against skin, which could hamper bleeding from the incision in the skin.

25 Claims, 9 Drawing Sheets

(51) Int. Cl.
 *A61B 5/145* (2006.01)
 *A61B 5/15* (2006.01)
 *A61B 5/157* (2006.01)

(56) References Cited

U.S. PATENT DOCUMENTS

| | | | |
|---|---|---|---|
| 3,640,393 A | 2/1972 | Hurtig | |
| 3,799,742 A | 3/1974 | Coleman | |
| 4,360,016 A | 11/1982 | Sarrine | |
| 4,627,445 A | 12/1986 | Garcia et al. | |
| 4,637,403 A | 1/1987 | Garcia et al. | |
| 4,787,398 A | 11/1988 | Garcia et al. | |
| 4,790,979 A | 12/1988 | Terminiello et al. | |
| 4,837,049 A | 6/1989 | Byers et al. | |
| 4,873,993 A | 10/1989 | Meserol et al. | |
| 4,920,977 A | 5/1990 | Haynes | |
| 4,924,879 A | 5/1990 | O'Brien | |
| 4,995,402 A | 2/1991 | Smith et al. | |
| 5,014,718 A | 5/1991 | Mitchen | |
| 5,029,583 A | 7/1991 | Meserol et al. | |
| 5,035,704 A | 7/1991 | Lambert et al. | |
| 5,054,499 A | 10/1991 | Swierczek | |
| 5,217,480 A | 6/1993 | Haber et al. | |
| 5,231,993 A | 8/1993 | Haber et al. | |
| 5,279,294 A * | 1/1994 | Anderson et al. | 600/322 |
| 5,290,420 A | 3/1994 | Matson | |
| 5,320,363 A | 6/1994 | Burnham | |
| 5,514,152 A | 5/1996 | Smith | |
| 5,571,132 A | 11/1996 | Mawhirt et al. | |
| 5,591,139 A | 1/1997 | Lin et al. | |
| 5,636,640 A | 6/1997 | Staehlin | |
| 5,682,233 A | 10/1997 | Brinda | |
| 5,700,695 A | 12/1997 | Yassinzadeh et al. | |
| 5,779,677 A | 7/1998 | Frezza | |
| 5,801,057 A | 9/1998 | Smart et al. | |
| 5,871,494 A | 2/1999 | Simons et al. | |
| 5,928,207 A | 7/1999 | Pisano et al. | |
| 5,938,679 A | 8/1999 | Freeman et al. | |
| 5,951,492 A | 9/1999 | Douglas et al. | |
| 5,971,941 A | 10/1999 | Simons et al. | |
| 6,036,924 A | 3/2000 | Simons et al. | |
| 6,048,352 A | 4/2000 | Douglas et al. | |
| 6,051,392 A | 4/2000 | Ikdeda et al. | |
| 6,071,251 A | 6/2000 | Cunningham et al. | |
| 6,071,294 A | 6/2000 | Simons et al. | |
| 6,120,676 A | 9/2000 | Heller et al. | |
| 6,235,539 B1 | 5/2001 | Carpenter | |
| 6,299,757 B1 | 10/2001 | Feldman et al. | |
| 6,315,738 B1 | 11/2001 | Nishikawa et al. | |
| 6,358,265 B1 * | 3/2002 | Thorne et al. | 606/181 |
| 6,537,257 B1 | 3/2003 | Wien | |
| 6,561,989 B2 | 5/2003 | Whitson | |
| 6,612,111 B1 | 9/2003 | Hodges et al. | |
| 6,616,616 B2 | 9/2003 | Fritz et al. | |
| 6,620,112 B2 | 9/2003 | Klitmose | |
| 6,783,502 B2 | 8/2004 | Orloff et al. | |
| 6,866,675 B2 | 3/2005 | Perez et al. | |
| 7,297,122 B2 | 11/2007 | Boecker et al. | |
| 7,299,081 B2 | 11/2007 | Mace et al. | |
| 7,488,298 B2 | 2/2009 | Patel et al. | |
| 7,540,998 B2 | 6/2009 | Terwilliger et al. | |
| 8,052,926 B2 | 11/2011 | Joseph et al. | |
| 2002/0052618 A1 | 5/2002 | Haar et al. | |
| 2002/0130042 A1 | 9/2002 | Moerman et al. | |
| 2002/0137998 A1 | 9/2002 | Smart et al. | |
| 2002/0168290 A1 | 11/2002 | Yuzhakov et al. | |
| 2002/0177763 A1 | 11/2002 | Burns et al. | |
| 2003/0018282 A1 | 1/2003 | Effenhauser et al. | |
| 2003/0028087 A1 | 2/2003 | Yuzhakov et al. | |
| 2003/0028125 A1 | 2/2003 | Yuzhakov et al. | |
| 2003/0050573 A1 * | 3/2003 | Kuhr et al. | 600/567 |
| 2003/0083685 A1 | 5/2003 | Freeman et al. | |
| 2003/0083686 A1 | 5/2003 | Freeman et al. | |
| 2003/0144608 A1 | 7/2003 | Kojima et al. | |
| 2003/0153939 A1 | 8/2003 | Fritz et al. | |
| 2003/0171699 A1 | 9/2003 | Brenneman | |
| 2003/0199893 A1 * | 10/2003 | Boecker et al. | 606/181 |
| 2003/0211619 A1 | 11/2003 | Olson et al. | |
| 2003/0212344 A1 | 11/2003 | Yuzhakov et al. | |
| 2003/0212345 A1 | 11/2003 | McAllister et al. | |
| 2003/0212346 A1 | 11/2003 | Yuzhakov et al. | |
| 2003/0212347 A1 | 11/2003 | Sohrab | |
| 2003/0223906 A1 | 12/2003 | McAllister et al. | |
| 2004/0034318 A1 | 2/2004 | Fritz et al. | |
| 2004/0064068 A1 | 4/2004 | DeNuzzio et al. | |
| 2004/0092842 A1 | 5/2004 | Boecker et al. | |
| 2004/0096959 A1 | 5/2004 | Stiene et al. | |
| 2004/0102717 A1 | 5/2004 | Qi | |
| 2004/0106941 A1 | 6/2004 | Roe et al. | |
| 2004/0120848 A1 | 6/2004 | Teodorczyk | |
| 2004/0127818 A1 | 7/2004 | Roe | |
| 2004/0127819 A1 | 7/2004 | Roe et al. | |
| 2004/0138588 A1 * | 7/2004 | Saikley et al. | 600/583 |
| 2004/0163987 A1 | 8/2004 | Allen | |
| 2004/0186394 A1 | 9/2004 | Roe et al. | |
| 2004/0193072 A1 | 9/2004 | Allen | |
| 2004/0193202 A1 | 9/2004 | Allen | |
| 2004/0206636 A1 | 10/2004 | Hodges et al. | |
| 2004/0225312 A1 | 11/2004 | Orloff et al. | |
| 2004/0236251 A1 | 11/2004 | Roe et al. | |
| 2005/0033341 A1 | 2/2005 | Vreeke et al. | |
| 2005/0036909 A1 | 2/2005 | Erickson et al. | |
| 2005/0139469 A1 | 6/2005 | Davies et al. | |
| 2005/0234368 A1 | 10/2005 | Wong et al. | |
| 2005/0245844 A1 | 11/2005 | Mace et al. | |
| 2005/0245845 A1 | 11/2005 | Roe et al. | |
| 2005/0245954 A1 | 11/2005 | Roe et al. | |
| 2005/0251064 A1 | 11/2005 | Roe | |
| 2005/0277850 A1 | 12/2005 | Mace et al. | |
| 2005/0283094 A1 | 12/2005 | Thym et al. | |
| 2006/0020228 A1 * | 1/2006 | Fowler | A61B 5/1411 600/583 |
| 2006/0047220 A1 | 3/2006 | Sakata et al. | |
| 2006/0079810 A1 | 4/2006 | Patel et al. | |
| 2006/0100542 A9 | 5/2006 | Wong et al. | |
| 2006/0100543 A1 | 5/2006 | Raney et al. | |
| 2006/0106411 A1 | 5/2006 | Schraga | |
| 2006/0174592 A1 | 8/2006 | Chan | |
| 2006/0216817 A1 | 9/2006 | Hoenes et al. | |
| 2006/0229532 A1 | 10/2006 | Wong et al. | |
| 2010/0130997 A1 * | 5/2010 | LeVaughn et al. | 606/172 |

FOREIGN PATENT DOCUMENTS

| | | |
|---|---|---|
| DE | 198 55 465 | 6/1999 |
| EP | 0 127 958 A2 | 5/1984 |
| EP | 0 199 484 B1 | 10/1986 |
| EP | 1 374 770 A1 | 1/2004 |
| EP | 1 402 812 A1 | 3/2004 |
| FR | 2 590 673 | 5/1987 |
| JP | 02-120655 | 5/1990 |
| JP | H04-194660 | 7/1992 |
| JP | H09-084781 | 3/1997 |
| JP | 09-089885 A1 | 4/1997 |
| JP | 09-168530 A1 | 6/1997 |
| JP | H09-285459 | 11/1997 |
| JP | H09-294737 | 11/1997 |
| JP | 09-313465 A1 | 12/1997 |
| JP | 10-005198 A1 | 1/1998 |
| JP | 10-005199 A1 | 1/1998 |
| JP | 10-005200 A1 | 1/1998 |
| JP | 10-014906 A1 | 1/1998 |
| JP | H10-024028 A1 | 1/1998 |
| JP | 10-033507 A1 | 2/1998 |
| JP | H10-033508 A1 | 2/1998 |
| JP | 2006-518629 A | 8/2006 |
| WO | WO 85/04089 A1 | 9/1985 |
| WO | WO 86/00513 A1 | 1/1986 |
| WO | WO 91/06855 A1 | 5/1991 |
| WO | WO 98/14125 | 4/1998 |
| WO | WO 2004/064636 A1 | 8/2004 |
| WO | WO 2004/066822 A2 | 8/2004 |

(56) References Cited

FOREIGN PATENT DOCUMENTS

| WO | WO 2004/075760 A1 | 9/2004 |
|---|---|---|
| WO | WO 2004/086970 A1 | 10/2004 |
| WO | WO 2005/084530 A2 | 9/2005 |
| WO | WO 2005/084545 A1 | 9/2005 |
| WO | WO 2005/084546 A3 | 9/2005 |
| WO | WO 2005/104948 A1 | 11/2005 |
| WO | WO 2005/104949 A1 | 11/2005 |
| WO | WO 2006/005503 A1 | 1/2006 |
| WO | WO 2006/092281 A2 | 9/2006 |

OTHER PUBLICATIONS

U.S. Appl. No. 11/620,931, filed Jan. 8, 2007.
U.S. Appl. No. 12/883,545 to Roe, Office Action mailed Oct. 13, 2011.
U.S. Appl. No. 12/883,545 to Steven N. Roe, Notice of Allowance mailed Jan. 16, 2015. 15 pages.

\* cited by examiner

DYNAMIC INTEGRATED LANCING TEST STRIP WITH STERILITY COVER

CROSS-REFERENCE TO RELATED APPLICATIONS

This application is a continuation of U.S. patent application Ser. No. 11/070,502 filed Mar. 2, 2005 now U.S. Pat. No. 7,815,579, which is hereby incorporated by reference.

BACKGROUND

The present invention generally relates to bodily fluid sampling devices and more specifically, but not exclusively, concerns an integrated lancing test strip with a lancet contained within a sterility sheet.

The acquisition and testing of bodily fluids is useful for many purposes, and continues to grow in importance for use in medical diagnosis and treatment, such as for diabetes, and in other diverse applications. In the medical field, it is desirable for lay operators to perform tests routinely, quickly and reproducibly outside of a laboratory setting, with rapid results and a readout of the resulting test information. Testing can be performed on various bodily fluids, and for certain applications, is particularly related to the testing of blood and/or interstitial fluid. Performing home based testing can be difficult for many patients, especially for patients with limited hand dexterity, such as the elderly or diabetics. For example, diabetics can sometimes experience numbness or tingling in their extremities, such as their hands, which can make self-testing difficult because they are unable to accurately position a test strip to collect the blood sample. In addition, wounds for diabetics tend to heal more slowly, and as a result, there is a desire to make incisions less invasive.

Recently, integrated lancing test strips have been developed in which a test strip is integrated with a lancet so as to form a single disposable unit. While these integrated units have somewhat simplified the collection and testing of fluid samples, there are still a number of issues that need to be resolved before a commercial unit can be implemented. One issue concerns maintaining the sterility of the lancet so as to minimize the risk of infection. In practice, conventional plastic or syringe type caps that are used to maintain the sterility of typical lancets cannot be incorporated with integrated lancing test strips for several reasons, especially for those designs with lancets that are moveable relative to the rest of the test strip. With typical syringe type caps, the cap encapsulates the lancet, and the cap is removed by pulling or twisting the cap off the lancet. However, the removal of the cap from the lancet without destroying or damaging the integrated device is difficult or even practically impossible. Moreover, automatic cap removal with such caps can be difficult. There is a trend to make lancets smaller or thinner so as to make less traumatic or less invasive incisions, which in turn makes self-monitoring less painful as well as promotes healing of the incision. However, due to their thinner nature, lancets are more prone to bending or are susceptible to other damage, especially when protective caps are removed. Further, the pulling or twisting action during cap removal can damage the test strip, like delicate electrodes in electrochemical type test strip, or can even result in the lancet being separated from the test strip.

Integrated devices have been proposed in which the lancet is encapsulated within a sterilized plastic body or a molded plastic plug that encloses one end of a lancet chamber. During lancing, the lancet pierces the body so as to extend from the body and lance the tissue. Such a design is suitable for automated systems because the lancet can be fired without the need to remove a protective cap. Given their bulky and rigid nature, these types of designs are not well suited for magazines, drums, cassettes, cartridges and the like, however. The encapsulating plastic creates a rather large profile, which does not allow a plurality of integrated devices to be packed in a tight package. Due to the somewhat rigid nature of the encapsulating material, the devices are too rigid by themselves for integration into a reel-to-reel type cassette design. Moreover, the injection molding required to manufacture these types of integrated devices can make the devices considerably more expensive as well as more difficult to assemble. Such designs can also limit how small the lancet can be because the lancet has to be rigid enough to still be able to puncture the seal.

Other integrated disposable designs have been proposed in which the entire unit is sealed within a protective packet. However, these designs require the entire disposable unit to be sterilized at the same time, which results in a whole host of difficulties. Unfortunately, sterilization techniques for lancets, such as radiation, adversely affect the chemical enzymes of the test strip. Hence, if left uncompensated, the accuracy of the test strip can be significantly hampered. To compensate for the changes that occur during sterilization, samples from sterilized lots are taken so that an adjustment or calibration value can be calculated for the lot. Before use, the calibration value for the lot is entered, either manually or automatically, into the meter to compensate for lot variations. Moreover, certain desirable sterilization techniques for lancets are impractical when the lancet and test strip are combined together because these techniques tend to damage or even destroy components on the test strip. In addition, undesirable cross contamination can occur between the lancet and the test strip when sealed in the same protective packet. For instance, components of the test strip, such as chemicals, biological components, adhesives and the like, can migrate within the packet onto the lancet, thereby possibly compromising the sterility of the lancet.

Ensuring that a sufficient amount of body fluid is collected during sampling is another issue that needs to be addressed before a viable commercial integrated lancing test strip can be implemented. It is desirable that the integrated device only lightly contacts the skin during fluid sampling. If the integrated device is pressed too hard against the skin, fluid flow from the incision can be blocked, which can occasionally lead to insufficient sample sizes. However, if the test strip is not touching at all, the test strip may be too far away for the blood drop to reach the capillary entrance of the test strip. When an insufficient amount of fluid for testing is collected, usually the integrated device has to be disposed of, and a new one is used to perform the test again. Further complicating this problem is that the elasticity of skin varies from person to person as well as varies between different body parts on the individual, which can create difficulties in locating the test strip. For example, the skin of a child is more elastic than that of the elderly. As a sampling device is pressed against the skin, the more elastic skin of the child tends to bow or pucker to a greater degree than the inelastic skin of the elderly. This variation of skin puckering height between individuals and body locations makes it difficult to design a meter that can accurately position a test strip so as to not contact the skin or only slightly contact the skin so as to not disturb fluid flow, but still be able to contact the drop of fluid from the incision for fluid collection purposes.

Thus, needs remain for further contributions in this area of technology.

SUMMARY

One aspect concerns an integrated lancing test strip that includes a test strip adapted to analyze body fluid and a packet coupled to the test strip. The packet includes an incision forming member to form an incision in tissue. A sterility sheet covers the packet to maintain sterility of the incision forming member and prevents cross-contamination between the test strip and the incision forming member. The sterility sheet allows the incision forming member to be sterilized separately from the test strip.

Another aspect concerns a technique in which a lancet packet is created by enclosing a lancet in a sterility sheet to form a sterile enclosure. The lancet is sterilized, and the integrated lancing test strip is assembled by attaching the lancet packet to a test strip after sterilizing the lancet.

A further aspect relates to a meter that includes a holder that is configured to hold a test strip. An adjustment mechanism cooperates with the holder to position the test strip relative to a tissue with an incision for reducing pressure applied against the tissue. By reducing the pressure applied against the tissue, flow constriction of body fluid from the incision is minimized as the body fluid is collected with the test strip.

Further forms, objects, features, aspects, benefits, advantages, and embodiments of the present invention will become apparent from a detailed description and drawings provided herewith.

DESCRIPTION OF THE SELECTED EMBODIMENTS

Figure 1:
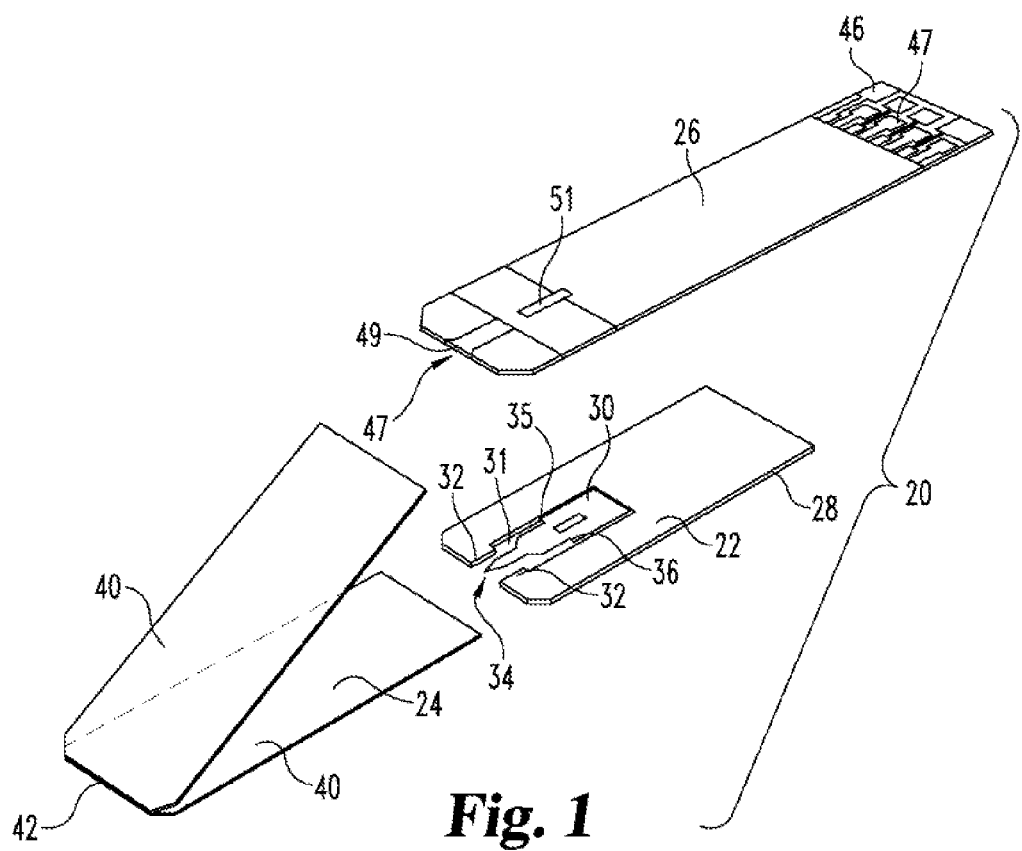
FIG. 1 is a first top exploded view of an integrated lancing test strip according to one embodiment.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. One embodiment of the invention is shown in detail, although it will be apparent to those skilled in the relevant art that some features that are not relevant to the present invention may not be shown for the sake of clarity.

One of the many embodiments of the present invention concerns an integrated lancing test strip that includes a unique sterility enclosure system. The integrated lancing test strip includes a lancet for forming an incision that is attached to a test strip for analyzing fluid from the incision. The lancet is at least partially enclosed by a sterility sheet, which maintains sterility of the lancet and simplifies manufacturing of the integrated lancing test strip. By enclosing the lancet in the sterility sheet, the lancet can be sterilized separately from the test strip, and then attached to the test strip after sterilization. As a result, this separate or modular construction of lancet and test strip allows the lancet to be sterilized without adversely effecting on chemical enzymes in the test strip that would affect the accuracy of the test results. With the sterility sheet, the integrated lancing test strip can also have a compact profile, which is well suited for incorporation of multiple integrated lancing test strips into magazines, drums, cassettes, cartridges and the like. Further, the sterility sheet minimizes cross-contamination between the lancet and the test strip before, during and after use. In one form, the integrated lancing test strip is loaded into a lancing device or meter that is configured to fire the lancet. The meter includes an adjustment mechanism that allows the user to adjust the position of the test strip relative to the skin during sampling. The adjustment mechanism allows users to compensate for a number factors, such as variations in skin elasticity, skin type, body part size and the pressure applied, to name a few. The adjustment mechanism can be used to compensate for these different conditions so as to allow the test strip to be positioned close enough to collect a fluid sample, but not too close so as to hinder fluid flow from the wound.

An integrated lancing test strip or device 20 according to one embodiment, among many, of the present invention will be described initially with reference to FIGS. 1, 2, 3, 4, 5 and 6. Referring to FIG. 1, the integrated lancing test strip 20 includes a lancet assembly or incision forming member 22 for forming an incision in tissue, a sterility sheet or foil 24 for maintaining the sterility of the lancet 22, and a test strip 26 for acquiring a body fluid from the incision. Both the lancet 22 and the test strip 26 in the illustrated embodiment are generally flat such that the integrated lancing test strip 20 has an overall flat appearance. By being flat, multiple integrated lancing test strips 20 can be incorporated into magazines, cassettes, drums, cartridges and the like, which allows a plurality of integrated lancing test strips 20 to be used without the need to individually load and/or dispose of used integrated devices 20. For example, the overall flat shape allows multiple integrated lancing test strips 20 to be stacked upon one another in a magazine or rolled around a reel in a cassette. Furthermore, the overall flat shape allows the integrated lancing test strip 20 to be manufactured with a continuous process in which layers of component materials can be layered to form contiguous strips of integrated lancing test strips 20 that can be cut to form individual units or remain attached for use in cassettes and the like. It should nonetheless be recognized that the integrated lancing test strip 20 in other embodiments can have a different overall shape.

Figure 5:
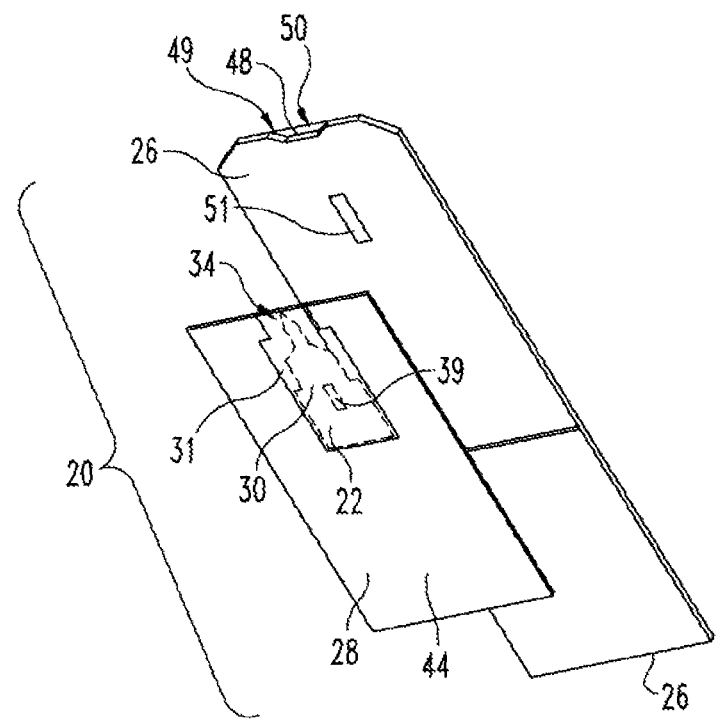
FIG. 5 is a bottom exploded view of the FIG. 1 integrated lancing test strip.

As can be seen in FIGS. 1 and 5, the lancet assembly 22 has a retaining element or guide member 28 that guides a piercing member or lancet 30 during lancing. The lancet 30 is slidably retained within a guide slot or opening 31 that is defined in a retainer 28. In the course of lancing, the guide slot 31 guides the movement of the lancet 30 during both extension and retraction. In the illustrated embodiment, the lancet 30 and the retainer 28 are separate components that are not directly attached to one another. Nevertheless, in other embodiments, the lancet 30 and the retainer 28 can be connected to one another. For example, the lancet assembly 22 can have breakable tabs that connect the lancet 30 to the retainer 28 so that the lancet 30 is held in place during manufacturing as well as prior to lancing, thereby reducing the risk of injury. During lancing, the tabs are broken to allow the lancet 30 to extend from the integrated lancing test strip 20. In another example, a spring for retracting the lancet 30 connects the retainer 28 to the lancet 30.

Figure 7:
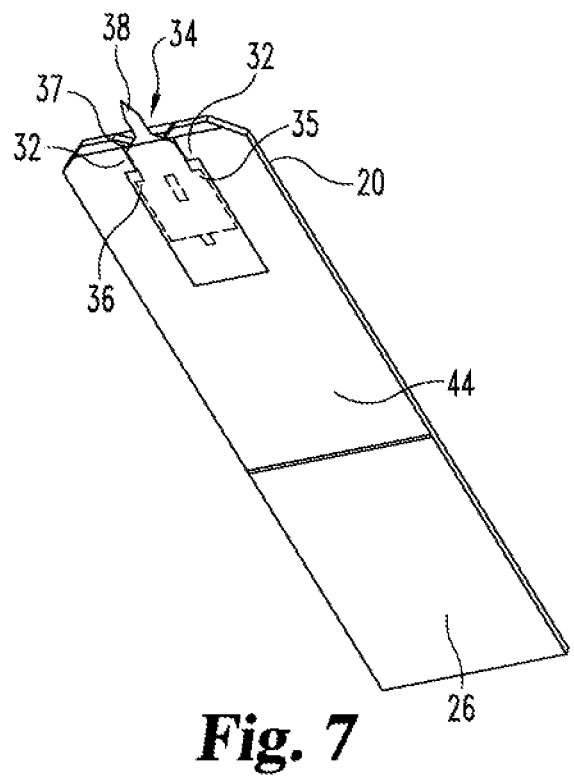
FIG. 7 is a second bottom perspective view of the FIG. 1 integrated lancing test strip with the lancet in the extended position.

As shown, end stops 32 of the retainer 28 extend inwardly at a slot opening 34 of the guide slot 31 so as to limit the movement of the lancet 30, thereby retaining the lancet 30 in the guide slot 31, as is depicted in FIG. 7. The lancet 30 has a body portion 35 with one or more stop edges 36, which are wider than the slot opening 34. When the lancet 30 is fully extended, the stop edges 36 of the lancet 30 can contact the end stops 32, and thus, limit the travel of the lancet 30. However, in other embodiments, the firing mechanism, which is used to fire the lancet 30, limits the travel of the lancet 30. A neck portion 37 of the lancet 30, which is slightly smaller that the size of the slot opening 34, extends from the body portion 35 of the lancet 30. During extension of the lancet 30, the neck 37 is received between the end stops 32 such that the end stops 32 can limit undesirable rotation of the lancet 30 as the tissue is punctured. Extending from the neck 37, the lancet 30 has a blade portion or tip 38 that is configured to cut tissue. In the illustrated embodiment, the lancet defines an engagement notch 39 for coupling the lancet 30 to a firing mechanism. In one form, the lancet assembly 22 is made at least in part of medical grade stainless steel, but it should be recognized that the lancet assembly 22 can be made of other materials, such as ceramics and/or plastics. Furthermore, it is contemplated that the guide member 28 and the lancet 30 can be made of different materials and/or manufactured separately. In one embodiment, the guide member 28 and lancet 30 are formed by a photo-etching technique in which a sheet of metal is photo-etched to form both the guide member 28 and the lancet 30, and in another embodiment, the lancet assembly 22 is manufactured via stamping. The lancet assembly 22 in still other embodiments can be manufactured through other techniques as would occur to those skilled in the art.

Figure 2:
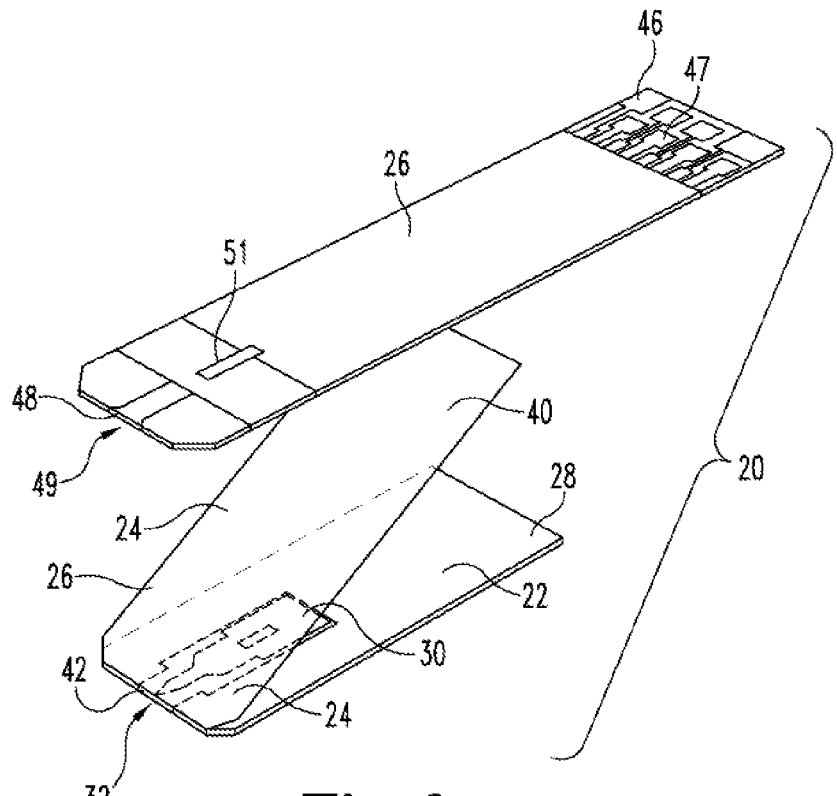
FIG. 2 is a second top exploded view of the FIG. 1 integrated lancing test strip.
Figure 3:
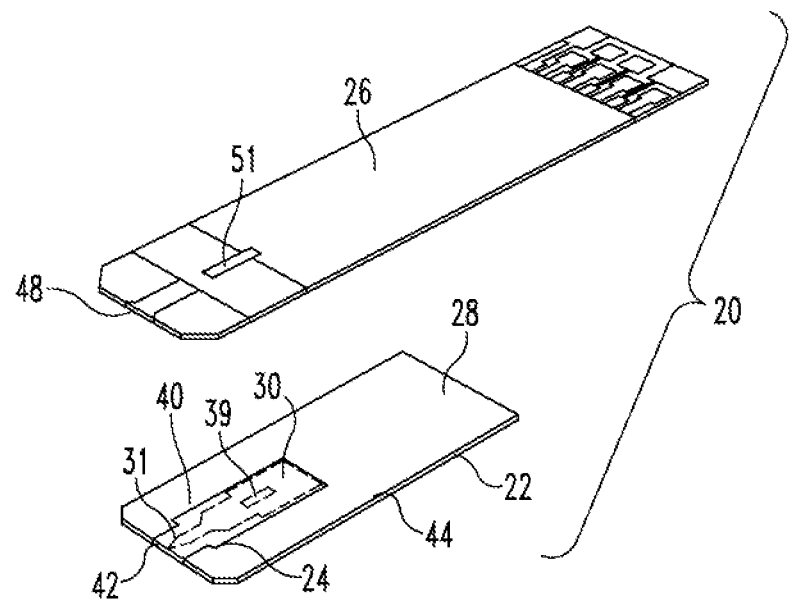
FIG. 3 is a third top exploded view of the FIG. 1 integrated lancing test strip.

With reference to FIGS. 1 and 2, after the lancet assembly 22 is formed, the lancet assembly 22 can be then packaged within the sterility sheet 24. As will be appreciated from the discussion below, the lancet assembly 22 can be packaged in the sterility sheet 24 before, during or after the lancet assembly 22 is sterilized. In the illustrated embodiment, the sterility sheet 24 is a sheet of metallic foil, and in another embodiment, the sterility sheet 24 is made of plastic. It should be recognized that the sterility sheet 24 can be made of other types of materials. During manufacturing, the sterility sheet 24 is folded into two flaps 40 with a crease or fold 42 in between, as is shown in FIG. 1. After folding, the lancet assembly 22 in FIG. 2 is sandwiched between the two folds 40 such that the crease 42 closes the slot opening 34 of the guide slot 31. As depicted in FIG. 3, the folds 40 are secured to the opposite (flat) sides of the lancet assembly 22 so that the lancet 30 is sealed inside the guide slot 31 with the slot opening 34 closed by the crease 42. In one form, an adhesive is used to secure the sterility sheet to the guide member 28. Adhesive is applied on the guide member 28 around the guide slot 31, but is not applied to the lancet 30 so that the lancet 30 is able to still slide within the guide slot 31. Although an adhesive is used in the illustrated embodiment, it should be understood that the sterility sheet 24 can be sealed with the guide member 28 in other manners, such as through heat sealing. In the illustrated embodiment, the edges of the folds 40 are not sealed together, but it is envisioned that in other embodiments the edges of the sterility sheet 24 can be sealed together so as to form a pocket that encloses the entire lancet assembly 22. In still yet another embodiment, instead of folding the sterility sheet 24, two sterility sheets 24 are joined together with the lancet assembly 22 sandwiched in between. For the sake of clarity, the drawings only show how an individual integrated lancing test strip 20 is formed, but it is contemplated that the integrated lancing test strips 20 in one embodiment are formed in a continuous process. In the continuous process, the sterility sheet 24 is a continuous band that is rolled off a reel and folded around a continuous band or belt of lancet assemblies 22 that are likewise rolled from a reel.

Once joined together, the lancet assembly 22 and the sterility sheet 24 form a lancet package or packet 44. As mentioned before, the lancet assembly 22 can be sterilized before being enclosed in the sterility sheet 24. The lancet assembly 22 can be sterilized through any number of sterilization techniques as would occur to those skilled in the art, such as through chemical, heat, and/or radiation sterilization techniques, to name a few. It should be understood that all or part of the lancet assembly 22 can be sterilized. For instance, only the lancet 30 and guide slot 31 can be sterilized, if so desired. In another embodiment, the lancet assembly 22 is sterilized after the lancet assembly 22 is packaged inside the lancet package 44. In one form, a radiation sterilization technique is used once the lancet 30 is enclosed by the sterility sheet 24. With the lancet package 44, sterilization of the lancet assembly 22 can occur without exposing the test strip to the undesirable affects of lancet sterilization.

In the illustrated embodiment, the test strip 26 is an electro-chemical type test strip. In one particular form, the test strip 26 includes a modified version of an ACCU-CHEK® brand test strip (Roche Diagnostics GmbH), but it is envisioned that other types of test strips can be used. For example, the test strip 26 in other embodiments can include an optical type test strip or can analyze fluid samples in other manners. At one end, the test strip 26 in the illustrated embodiment includes a connection portion 46 with electrical contacts 47 that transmit sample readings to a meter. Opposite the connection portion 46, the test strip 26 has a capillary channel 48 with a capillary opening 49 that is configured to draw a body fluid sample from an incision formed by the lancet 30 via capillary action. As should be appreciated, the test strip 26 inside the capillary channel 48 includes an analysis region that includes electrodes, such as working, counter and reference electrodes, and reagents for analyzing the fluid sample. In one form, the connection portion 46 is connected to a meter, and the sample readings from the electrodes in the analysis region are transmitted to the meter via the electrical contacts.

Figure 6:
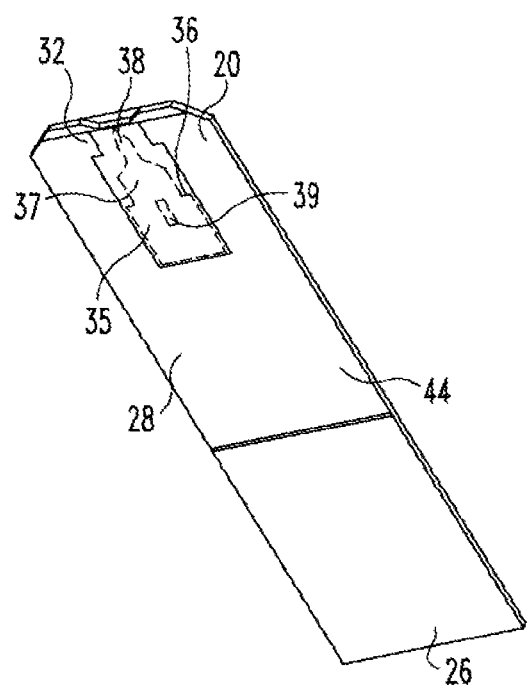
FIG. 6 is a first bottom perspective view of the FIG. 1 integrated lancing test strip with the lancet in a retracted position.

Looking at FIGS. 5 and 6, the sterilized lancet package 44 is attached to the test strip 26 to form the integrated lancing test strip 20. As depicted, the lancet package 44 is attached at the end of the test strip 26 proximal to the capillary opening 49 of the capillary channel 48. In particular, the guide slot opening 34 of the lancet assembly 22 and the capillary opening 49 of the test strip 26 are positioned near one another in a side-by-side relationship so that, when the lancet 30 forms the incision, the capillary channel opening 49 is positioned in close proximity to collect the body fluid. The test strip 26 is attached to the exterior of the sterility sheet 24 enclosing the lancing member 22 to complete the integrated test strip 20. The test strip 26 in one form is attached to the lancet package 44 through an adhesive, but it should be recognized that the test strip 26 and lancet package 44 can be attached in other manners. In one form, the lancet package 44 is attached to the test strip 26 such that the end edges of both are aligned with another. However, in other embodiments the edges of the lancet package 44 and the test strip 26 can be offset from one another. For example, the edge of the lancet package 44 in the illustrated embodiment, as is demarked by crease 42, is recessed slightly from the edge of the test strip 26 at the capillary opening 49. By having the lancet package 44 recessed, fluid flow to the capillary channel opening 49 is promoted. In another example, the sterility sheet 24 is positioned such that the crease 42 extends past the edge of the test strip 26. With this example, all or part of the sterility sheet 24 can be hydrophobic and/or hydrophilic so as to direct fluid flow towards the capillary channel 48. In one particular form, the sterility sheet 24 extends from the test strip 26 such that the sterility sheet 24 acts like a flexible wicking flag that draws fluid into the capillary channel 48.

To draw the body fluid towards the capillary channel opening 49 and away from the lancet 30, the test strip 26 in the illustrated embodiment has a fluid direction notch 50 facing the lancet package 44. In order to enhance fluid flow towards the capillary channel opening 49, the sterility sheet 24 can be treated and/or made to be hydrophobic. With the sterility sheet 24 being hydrophobic, the sterility sheet can squeegee or wipe body fluid from the lancet 30 as the lancet 30 retracts back inside the guide slot 31. It is thought that the wiping action of the sterility sheet 24 increases the amount of body fluid available for sampling as well as makes the lancet 30 cleaner for disposal purposes. As noted before, with the lancet 30 sealed in the lancet package 44, the risk of cross-contamination between the lancet 30 and the test strip 26 is reduced.

Figure 4:
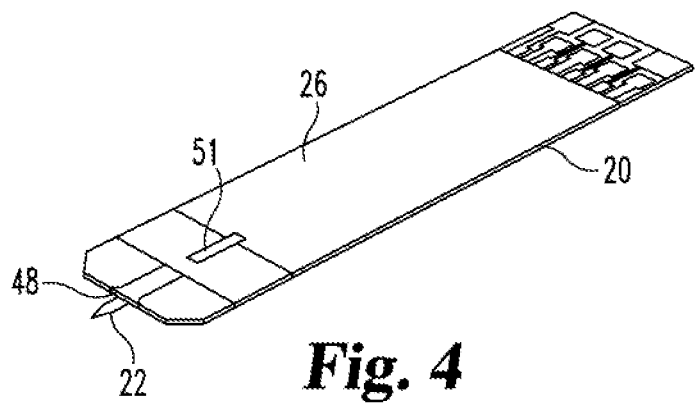
FIG. 4 is a top perspective view of the FIG. 1 integrated lancing test strip with its lancet in an extended position.

In FIGS. 3 and 4, the test strip 26 further defines a relief slot 51 through which a blade tip of a cam arm extends when engaging the lancet 30 during loading and firing. In addition, the relief slot 51 can be used to vent air from the capillary channel 48 as fluid is collected. The length of the relief slot 51 generally approximates the length of the lancing stroke of the firing mechanism used to actuate the lancet 30. When the lancet package 44 is attached to the test strip 26, the engagement notch 39 on the lancet 30 is aligned with the relief slot 51 in the test strip 26. As will be described in greater detail below, the blade tip of a cam arm for the firing mechanism extends through the engagement notch 39 of the lancet 30 as well as into the relief slot 51. When doing so, the blade tip pierces the sterility sheet 24. During lancing, the cam arm via the blade extends and retracts the lancet 30 relative to the test strip 26. As the lancet 30 extends, the tip 38 of the lancet 30 pierces the sterility sheet 24 at crease 42, as is illustrated in FIGS. 4 and 7. In one form, the sterility sheet 24 at the crease 42 is weakened so as to aid in puncturing by the lancet 30, but in other forms, the crease 42 is not weakened. Once the lancet 30 is retracted back inside the guide slot 31, as is shown in FIG. 6, the two flaps 40 of the sterility sheet 40 can hold the lancet 30 inside through friction. By engaging the lancet 30 in such a manner, the risk of accidental puncturing by the integrated lancing test strip 22 is reduced because it is more difficult to manually and/or accidentally actuate the lancet 30. It should be recognized that the lancet assembly 22 can incorporate other structures for engaging the lancet 30. For instance, the engagement notch 39 in the lancet 30 can be replaced with a protrusion or knob. It is also contemplated that the lancet can be fired through non-mechanical and/or non-contact techniques, which do not require the puncturing of the sterility sheet 24. As an example, the lancet 30 in another embodiment is magnetized and fired magnetically through a voice coil driver. With the lancet 30 enclosed in the sterility sheet 24 both before and after lancing, the risk of contamination is reduced, and the risk of accidental injury is likewise reduced.

Figure 8:
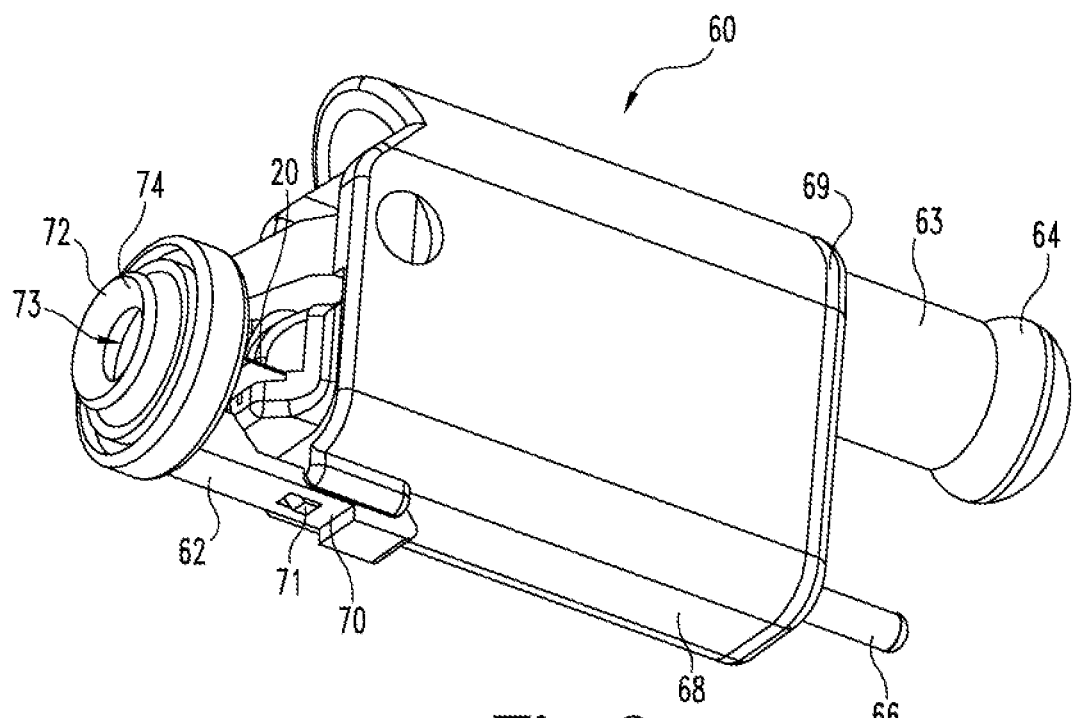
FIG. 8 is a first front perspective view of a meter when the FIG. 1 integrated lancing test strip is loaded.
Figure 9:
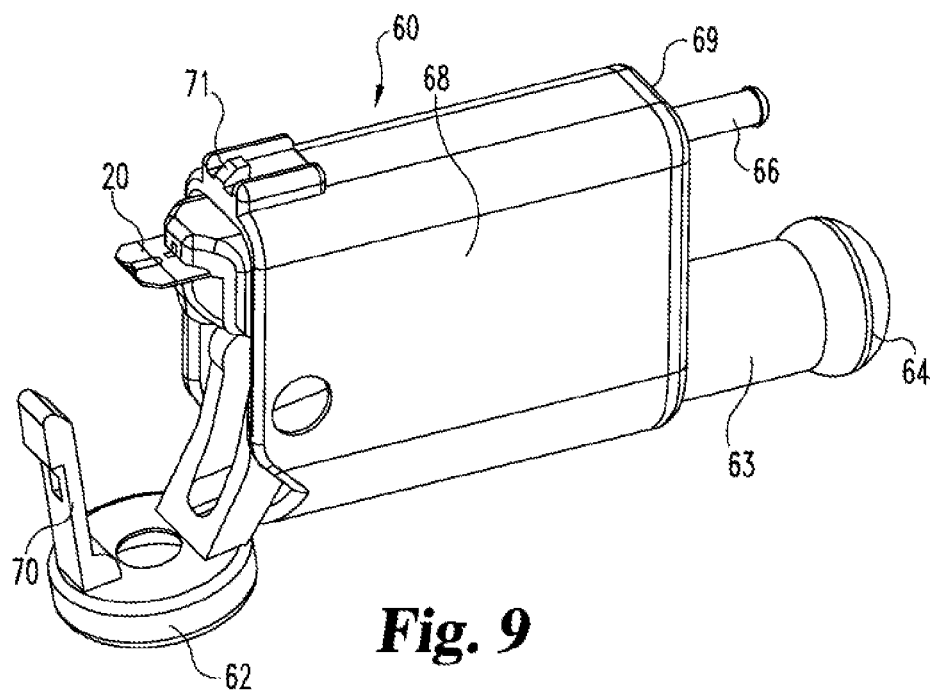
FIG. 9 is a second front perspective view of the FIG. 8 meter during loading of the FIG. 1 integrated lancing test strip.
Figure 10:
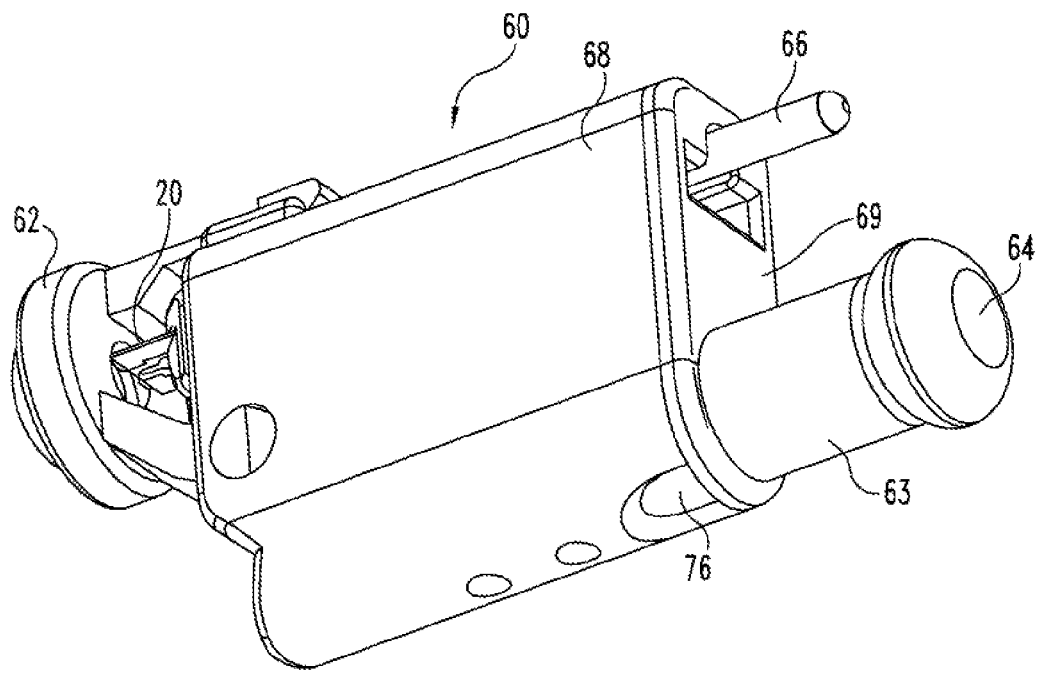
FIG. 10 is a rear perspective view of the FIG. 8 meter.

A lancing device or meter 60, according to one embodiment, that is configured to lance tissue and collect as well as analyze fluid from the tissue with the integrated lancing test strip device 20 is illustrated in FIGS. 8, 9 and 10. In one embodiment, the meter 60 includes a display or other types of output means for outputting sample readings from the integrated lancing test strip 20. The meter 60 in the illustrated embodiment is configured to adjust the relative position of the test strip 26 from the skin during sampling. Referring to FIG. 8, the lancing device 60 has a cap portion 62 that is configured to contact tissue and a firing mechanism 63 with a cocking knob 64 for the cocking of the firing mechanism 63. The lancing device 60 further includes an adjustment control or mechanism 66 for adjusting the sampling position of the test strip 26 and a housing 68 with an end plate 69 that houses the components of the lancing device 60. As shown in FIGS. 8 and 9, the cap 62 is hingedly coupled to the housing 68 so that the cap 62 can be pivoted away to permit loading of the integrated lancing test strip 20 (FIG. 9). The cap 62 further includes a latch 70 with an opening that engages a lock tab 71 on the housing 68 such that the cap 62 is locked in place once the integrated lancing test strip 20 is loaded, as is depicted in FIG. 8. An expression member 72 is coupled to the cap 62, and the expression member 72 defines a sampling opening 73 through which the lancet 30 lances the skin and the test strip 26 collects fluid from the incision. In the embodiment shown, the expression member 72 is ring-shaped and is threadedly coupled to the cap 62, so that the expression member 72 is able to move in a telescoping fashion, thereby allowing height adjustment of the expression member 72 relative to the cap 62. The proximity of the test strip 26 to the target tissue can be adjusted by the user, by turning the expression member 72. This adjustment can be individually based on a number of factors such as the size of the body part being sampled and how hard the user typically presses against the skin. Around the sampling opening 73, the expression member 72 has a skin or tissue contacting surface 74 that is configured to contact the skin during lancing and sampling. In the illustrated embodiment, the skin contacting surface 74 is inwardly angled so as to promote expression of fluid from the incision as the cap 62 is pressed against the skin.

As can be seen in FIG. 10, the firing mechanism 63 includes a firing button 76 that is pressed by the user in order to actuate the firing mechanism 63, once cocked. In the illustrated embodiment, the firing mechanism 63 includes a spring-powered type firing mechanism of the type as generally known to those skilled in the art. To cock the firing mechanism, the cocking knob 64 is pulled and the potential energy from pulling the knob 64 is stored by the springs in the firing mechanism 63. When the user presses the firing button 76, the potential energy stored in the springs is released so that the energy is used to fire the lancet 30. After the lancet 30 is fully extended, the firing mechanism 63 recoils so as to retract the lancet 30 from the target tissue. It should be recognized that the lancing device 60 can incorporate other types of firing mechanisms as known to those skilled in the art, like electrical and/or pneumatic type firing mechanisms, for example.

Figure 11:
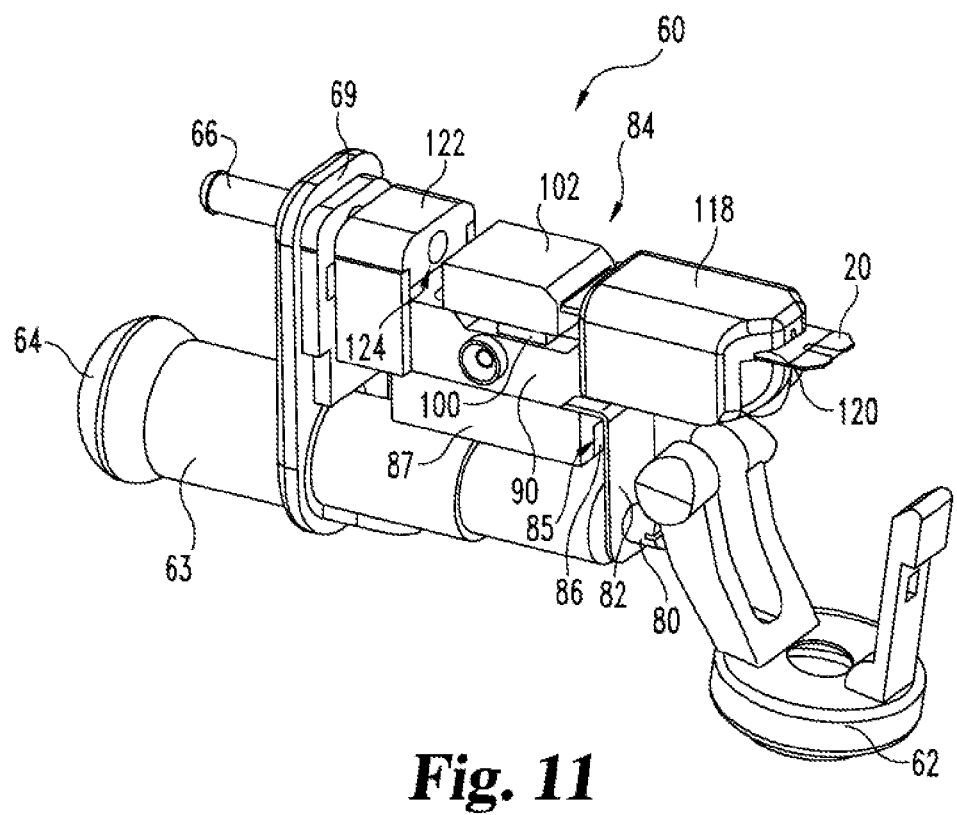
FIG. 11 is a perspective view of the FIG. 8 meter with its housing removed.
Figure 12:
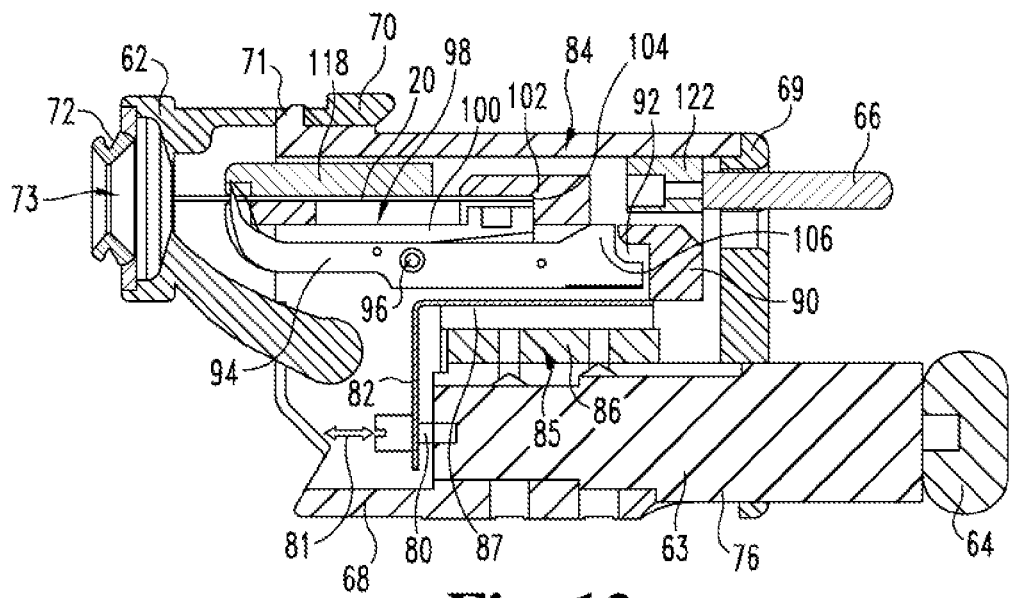
FIG. 12 is a cross-sectional view of the FIG. 8 meter.

FIG. 11 shows the lancing device 60 with the housing 68 partially removed, and FIG. 12 shows a cross-sectional view of the lancing device 60. As shown, the firing mechanism 63 extends through and is secured to the end plate 69 of the housing 68. Opposite the cocking knob 64, the firing mechanism 63 has an actuation arm 80 that is configured to extend from the firing mechanism 63 upon lancing and subsequently retract, as is indicated by double arrow 81. In the illustrated embodiment, the actuation arm 80 is in the form of a rod, but the actuation arm 80 as well as the rest of the firing mechanism 63 in other embodiments can have a different shape than is shown. To give the lancing device 60 a compact configuration, the lancing device 60 includes a drive connector 82 that is connected to the actuation arm 80 of the firing mechanism 63. The drive connector 82 is configured to transmit force from the firing mechanism 63 to an actuation assembly 84, which physically fires the integrated lancing test strip 20. In the illustrated embodiment, the drive connector 82 is L-shaped so that the firing mechanism 63 and the actuation assembly 84 can be oriented in a side-by-side relationship so as to give the lancing device 60 an overall compact shape. The actuation assembly 84 includes a bearing block 87 with a bearing channel 85 that receives a bearing rib 86. The bearing block 87 is connected to the drive connector 82, and the bearing rib 86 is secured to the housing 86 via the firing mechanism 63. As the actuation arm 80 of the firing mechanism 63 extends and retracts, the bearing block 87 slides relative to the bearing rib 86.

Figures 13, 14:
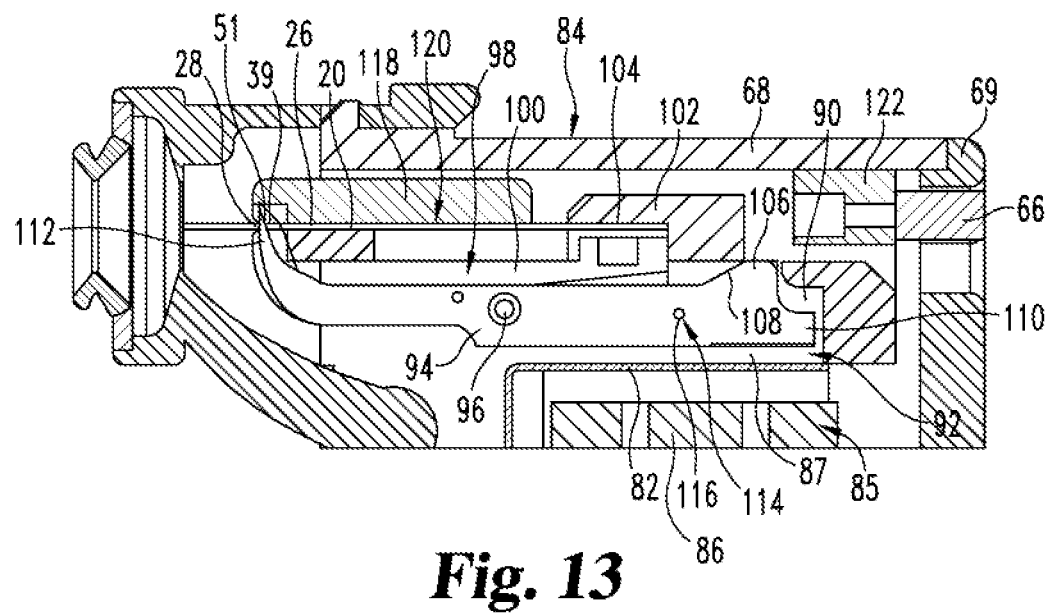
FIG. 13 is an enlarged cross-sectional view of an actuation mechanism in the FIG. 8 meter.
FIG. 14 is a perspective view of the FIG. 8 meter as the FIG. 1 integrated lancing test strip is loaded.

With reference to FIGS. 12 and 13, the actuation assembly 84 includes a strip holder 90 for holding and actuating the integrated lancing test strip 20. The strip holder 90 defines a cam arm channel 92 in which a cam arm 94 is pivotally disposed. As depicted, the cam arm 94 is pivotally coupled to the holder 90 via a pivot pin 96, but it should be realized that the cam arm 94 and the holder can be pivotally coupled in other manners. Looking at FIG. 13, the holder 90 further defines a slide connector arm cavity 98 in which a connector arm 100 is slidably disposed. Connector arm 100 is connected to a connector block or member 102 such that the connector block 100 is able to slide relative to the holder 90. The connector block 102 defines a connector slot 104 that is shaped to receive the connection portion 46 of the test strip 26. Inside the connector slot 104, the connector block 102 in one form includes electrical contacts that touch the contacts 47 on the test strip 26 in order to transmit readings from the test strip 26 to the meter 60.

At one end, the cam arm 94 has a cam member or portion 106 with a cam surface 108 that is angled or tapered to engage the connector block 102. Near the cam portion 106, the cam arm 94 has a limit tab 110 that is configured to contact the holder 90 in order to limit the rotation of the cam arm 94. Opposite the cam portion 106, the cam arm 94 has a lancet engagement blade 112 that is sharp in order to pierce the sterility sheet 24 of the integrated lancing test strip 20. During loading of the integrated lancing test strip 20, the connector block 102 is pushed further inside the lancing device 60 towards the cam portion 106 of the cam arm 104. When the connector block 102 engages the cam surface 108 of the cam portion 106, the cam arm 94 is rotated such that the blade 112 punctures the sterility sheet 24. After cutting the sterility sheet 24, the blade 112 extends into the engagement notch 39 of the lancet 30 so that the cam arm 94 is able to hold the lancet 30 during lancing. The relief notch 51 in the test strip 26 ensures that the blade 112 extends completely through the engagement notch 39 so that the cam arm 94 fully engages the lancet 30. In the illustrated embodiment, the integrated lancing test strip 20 is loaded with the lancet assembly 28 facing the blade 112 so that the blade 112 first extends through the engagement notch 39 of the lancet 30 before extending through the relief notch 51 of the test strip 26. It is contemplated that in other embodiments the integrated lancing test strip 20 is flipped so as to be oriented in the opposite manner. That is, the test strip 26 faces the blade 112 during loading so that the blade engages the lancet 30 by extending first through the relief notch 51 in the test strip 26. In the illustrated embodiment, the holder 90 has one or more detent mechanism 114 that engage one or more detent openings 116 in the cam arm 94 so as to hold the cam arm 94 in position during lancing. In one embodiment, the detent mechanism 114 includes a ball-type detent, but as should be recognized, other types of mechanisms can be used to hold the cam arm 94 in position. In the illustrated embodiment, the blade 112 is hooked shaped or angled so as to permit easy removal of the integrated lancing test strip 20 subsequent to sampling and/or testing. Near the blade 112, a cover 118 is secured to the holder 90. Together, the cover 118 and the holder 90 define a strip holder slot 120 that receives and holds the integrated lancing test strip 20 during both lancing and sampling. Referring again to FIG. 12, the strip holder slot 120 is aligned with the sampling opening 73 in the cap 70 so that the integrated lancing test strip 20 is able to sample fluid in an unencumbered manner.

As mentioned before, the adjustment control 66 allows for the adjustment of the position of the test strip 26 relative to the skin during sampling so that the test strip 26 does not press too hard against the skin so as to constrict bleeding from the incision. As illustrated in FIGS. 11 and 12, the adjustment control 66 is threadedly secured to the end plate 69, and the adjustment control 66 extends through the end plate 69 and engages a limit stop 122, which faces the connector block 102. At least a portion of the stop 122 is received in a guide channel 124 (FIG. 11) so as to prevent rotation of the stop 122 as the adjustment control 66 is turned. By twisting the adjustment control 66, the distance between the stop 122 and the connector block 102 can be increased or reduced. During operation, the stop 122 limits the travel of the connector block 102, which in turn limits how far the test strip 26 is able to retract away from the target tissue, and hence, control the distance between the capillary opening 49 of the test strip 26 and the surface of the target tissue. As a result, the test strip 26 can be kept in close proximity to the tissue or slightly contact the tissue without the risk of hindering blood flow from the wound. It is contemplated that the adjustment mechanism 66 can includes other types of adjustment mechanisms. By way of a non-limiting example, the adjustment mechanism in another form can includes an electrical motor that moves the stop 122. The position of the stop 122 can be adjusted manually by the user through one or more buttons on the meter 60 or can be automatically adjusted by the meter 60. In one form, the meter 60 automatically adjusts the position of the test strip 26 by sensing the relative position of the skin via a sonar-type detector and/or via an optical sensor.

The integrated lancing test strip 20 can form an incision and collect body fluid from the incision using a number of techniques. In one technique, the test strip 26 is held fixed in relation to the lancing device 60, and the lancet 30 is moved forward and backwards to pierce the skin. In another technique, the lancet 30 is held fixed to the test strip holder 90 while the test strip 26 can move with the connector block 102. When the test strip 26 contacts the skin, the test strip 26 is pushed back by the skin such that the lancet 30 is exposed so as to pierce the skin or other tissue. With the test strip 26 contacting the skin, variations in skin height do not significantly affect the penetration depth of the lancet 30.

Figure 15:
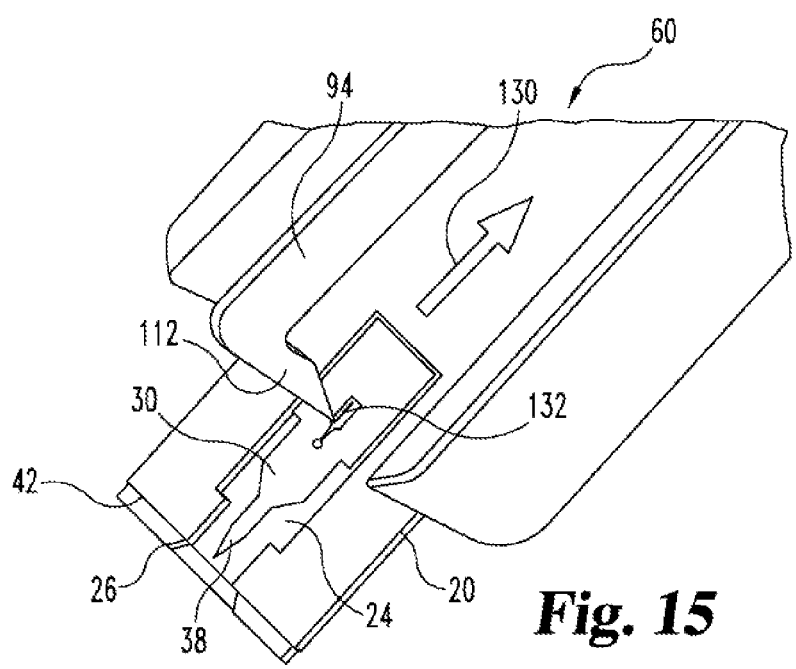
FIG. 15 is a perspective view of a cam arm of the FIG. 8 meter engaging the FIG. 1 integrated lancing test strip.

To aid in understanding and appreciating the features of the integrated lancing test strip 20 and the meter 60, a technique for sampling fluid will be described with reference to FIGS. 14, 15, 16, 17 and 18. From the previous discussion, it however should be recognized that the body fluid can be sampled in other manners. With reference to FIG. 14, the integrated lancing test strip 20 is loaded by pushing the integrated lancing test strip 20 into the meter 60, as is shown by direction arrow 130. The connection portion 46 of the test strip 26 is received in the connector block 102, as is depicted in FIG. 13. While the integrated lancing test strip 20 is pushed farther inside the meter 60, the connector block 102 engages the cam surface 108 on the cam arm 94 such that the cam arm 94 pivots in a teeter-tooter fashion. The pivoting of the cam arm 94 causes the blade 112 on the cam arm 94 to pierce the sterility sheet 24 on the integrated lancing test strip 20 so that the blade 112 engages the engagement notch 39 in the lancet 30, as is depicted in FIG. 15. Once the cam arm 94 is rotated to engage the lancet 30, the detent mechanism 114 locks the position of the cam arm 94 so as to prevent accidental disengagement during lancing. While the integrated lancing test strip 20 is pushed farther inside the meter 60 (FIG. 15), as indicated by direction arrow 130, the blade 112 on the cam arm 94 forms a slit 132 in the sterility sheet 24. The slit 132 in the sterility sheet 24 allows for smooth movement of the lancet 30 and cam arm 94 during retraction. Once the connector 102 contacts the stop 122, the integrated lancing test strip 20 is fully loaded.

Figure 16:
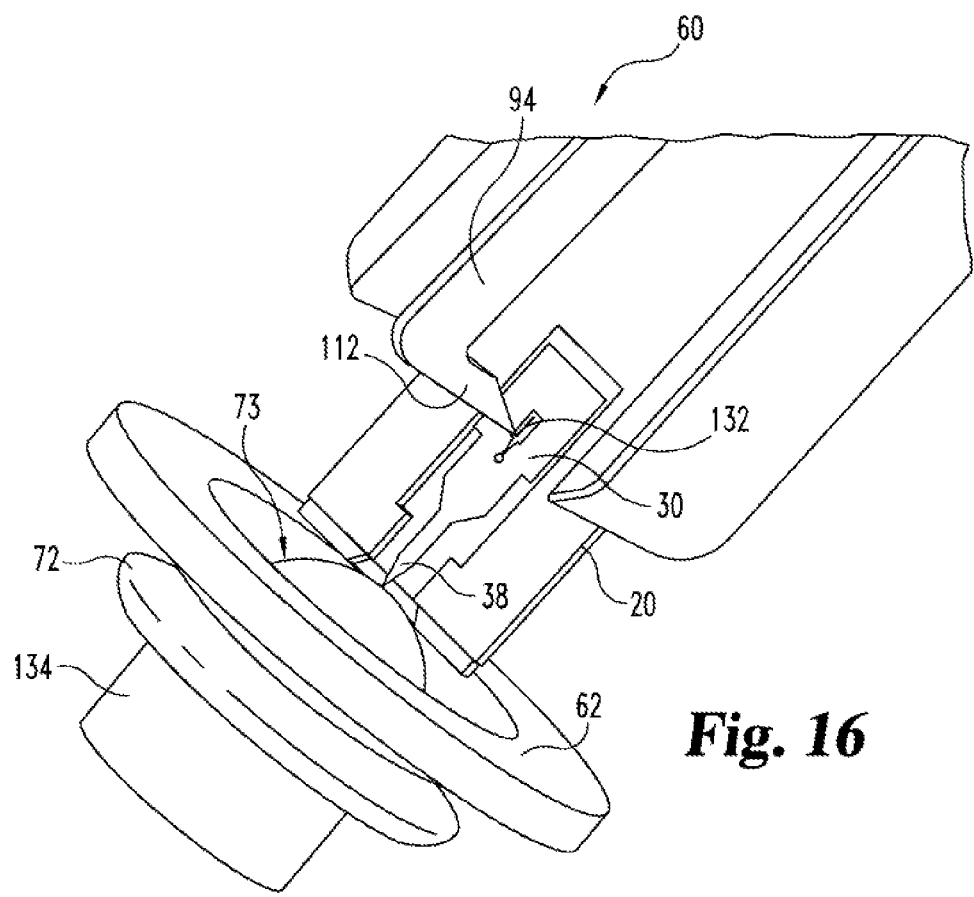
FIG. 16 is a perspective view of the FIG. 8 meter and the FIG. 1 integrated lancing test strip prior to lancing.

In one embodiment, when the integrated lancing test strip 20 is fully loaded, the lancet 30 remains completely sealed inside the pouch formed by the sterility sheet 24 until lancing is initiated. In another embodiment, like the one shown in FIG. 15, the tip 38 of the lancet 30 slightly pierces the crease 42 of the sterility sheet 42 once the integrated lancing test strip 20 is fully loaded. To prevent accidental injury, the tip 38 of the lancet 30 does not however extend past the edge of the test strip 26. During loading of the meter 60, the cap 62 of the meter 60 is pivoted out of the way in the manner as is shown in FIG. 9. Once loaded, the cap 62 of the meter 60 is rotated and locked into a firing position, like is illustrated in FIG. 8. The firing mechanism 63 is cocked by pulling the knob 64. Before lancing is initiated, the sampling opening 73 of the cap 62 is positioned over a targeted body part or tissue 134, such as the skin of a finger, which is shown in FIG. 16, so that the expression member 72 contacts the body part 134. It should be recognized that the firing mechanism 63 can be cocked before or after the meter 60 is placed against the targeted body part 134.

Figure 17:
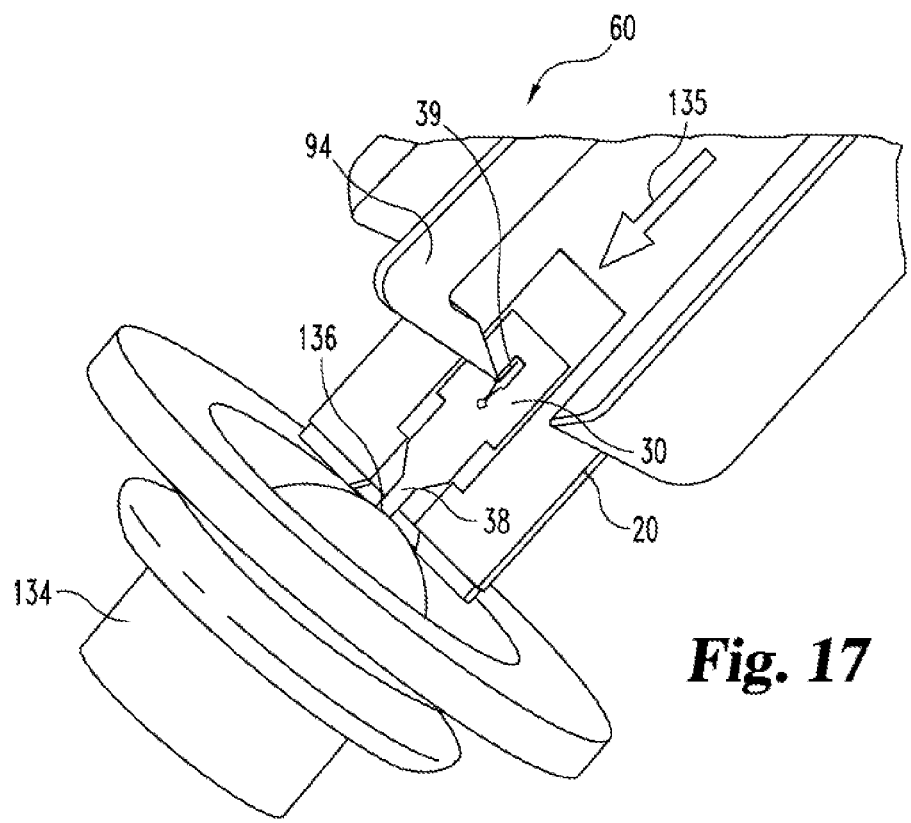
FIG. 17 is a perspective view of the FIG. 8 meter and the FIG. 1 integrated lancing test strip during lancing.

Referring to FIGS. 10, 12 and 17, the user presses the fire button 76 of the firing mechanism 63 to initiate lancing. Upon firing, the actuation arm 80 (FIG. 12) extends from the firing mechanism 63, and the drive connector 82 transmits this extension force to the holder 90, whereby the holder 90 likewise moves towards the body part 134. As the holder 90 moves, the integrated lancing test strip 20 also moves. Since the cam arm 94 is attached to the holder 90 and the blade 112 of the cam arm 94 is secured to the lancet 30, the lancet 30 extends along with the rest of the integrated lancing test strip 20 towards the body part 134. Once the test strip 20 contacts the body part 134, the frictional forces that caused the test strip 26 to move with the holder 90 are unable to move the test strip 26 any further so that the test strip 26 rests against the tissue 134. Although the test strip 26 stops moving, the lancet 30 continues to move because of the engagement of the lancet 30 with the cam arm 94 of the still moving holder 90. Consequently, upon contacting the tissue 134, the test strip 26 is pushed back, and the tip 38 of the lancet 30 is exposed such that the tip 38 penetrates the tissue 134, as is depicted in FIG. 17. As indicated by direction arrow 135 in FIG. 17, the lancet 30 continues to extend until the firing mechanism 63 reaches its maximum stroke length. After forming an incision 136 in the tissue 134, the firing mechanism 63 retracts the holder 90, which in turn retracts the lancet 30 as well as the rest of the integrated lancing test strip 20. In another embodiment, the test strip 26 does not contact the skin during lancing, but rather, the tip 38 of the lancet is exposed by contacting the backside of the expression member 72.

Figure 18:
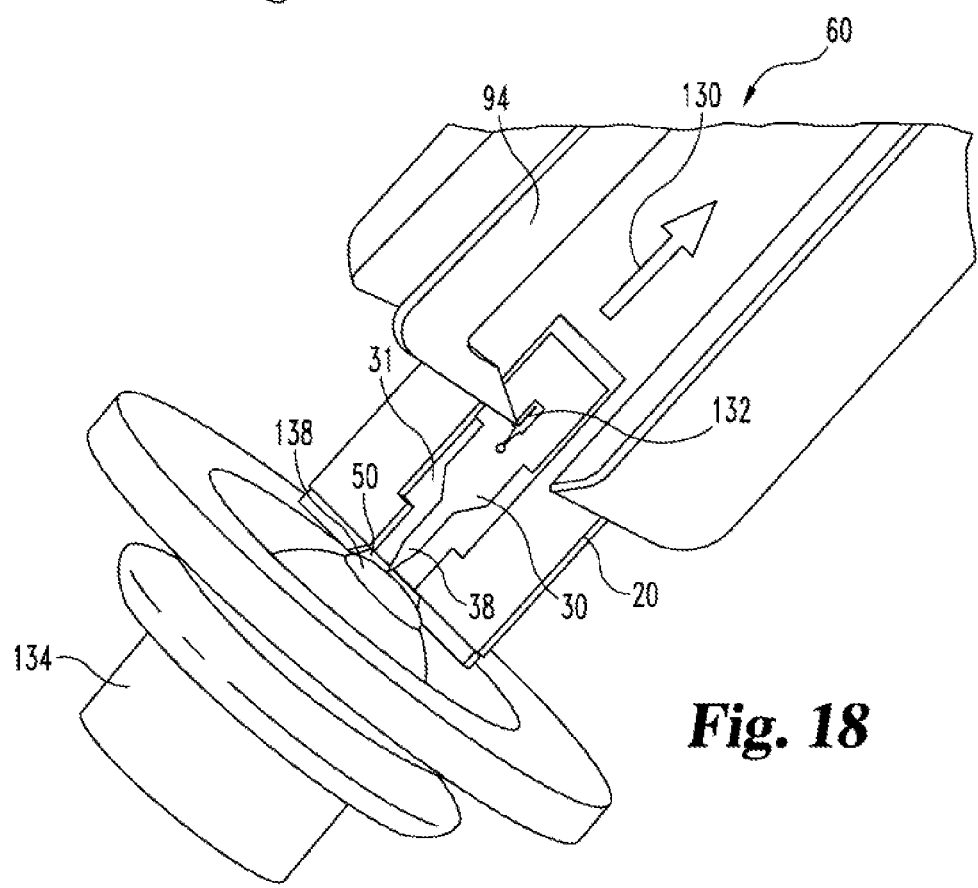
FIG. 18 is a perspective view of the FIG. 8 meter and the FIG. 1 integrated lancing test strip during sampling.

As mentioned previously, the adjustment control 66 via the stop 122 controls the position of the test strip 26 relative to the tissue 134 so as to prevent constriction of fluid flow from the incision 136. During retraction of the holder 90, the integrated lancing test strip 20 along with the connector block 102 retract until the connector block 102 contacts the stop 122, thereby limiting the retraction of the test strip 26. Although the test strip 26 stops retracting, the cam arm 94 along with the lancet 30 continues to retract in direction 130, as is shown in FIG. 18, such that the lancet 30 retracts inside the guide slot 31 of the lancet assembly 22. Once retracted, the lancet 30 can be received inside the sterility sheet 24 so as to reduce the risk of accidental injury as well as biological contaminate exposure during disposal. In one form, the sterility sheet 24 can act like wiper blades so as to wipe body fluid 138 or other contaminants from the lancet 30 so that the integrated lancing test strip 20 is generally cleaner after use as well as increase the amount of body fluid 138 that is available for testing. In one example, the sterility sheet 24 is hydrophobic to enhance the ability to wipe body fluid 138 from the lancet 30.

Looking at FIG. 18, the edge of the test strip 26 is spaced slightly away from the surface of the tissue 134, but is still positioned close enough to collect the body fluid 138 from the incision 136. It should be noted that the user can twist the adjustment control 66 so that the integrated lancing test strip 20 lightly contacts the tissue 134 during sampling or space the test strip 26 farther away, if so desired. Moreover, it is envisioned that other components, such as bendable wicking flags and the like, can also contact the skin during sampling. The lancet 30 is recessed behind capillary opening 49 so the lancet 30 does not contact the tissue 134 when the lancet 30 is retracted and is far enough behind capillary opening 49 so the drop of body fluid 138 will find the capillary opening 49 of the test strip 26 before the body fluid 138 finds the opening formed by the lancet 30 in the sterility sheet 24. For instance, the lancet 30 in one embodiment is retracted 0.5 to 0.75 mm behind the capillary opening 49. By recessing the lancet package 44 in the manner illustrated, expression of body fluid 138 from the incision 136 is not hindered by the presence of the lancet 30. If needed, the user can press the meter 30 against the tissue 134 such that the expression member 72 expresses the body fluid 138 from the incision 136. Once the body fluid 138 starts flowing from the incision 134, the capillary channel 49 of the test strip 26 collects the fluid 138. As previously noted, the test strip 26 has the notch 50 that directs the fluid flow towards the opening 39 of the capillary channel 49 and away from the lancet 30.

After a sufficient amount of the body fluid 138 is collected, the fluid 138 is analyzed with the test strip 26, and the test results are shown on a display on the meter 60 and/or transmitted to another device, like a computer for further analysis. Once the integrated lancing test strip 20 has been used, the integrated strip 20 is removed from the meter 60 for disposal. During removal of the integrated lancing test strip 20, the cap 62 is pivoted out of the way to allow the user to gain access to the integrated lancing test strip 20, as is depicted in FIG. 9. To remove the integrated strip 20, the user pulls the integrated strip 20 out of the meter 60. With reference to FIG. 13, as the user pulls the integrated strip 20, the hooked or angled shape of the blade 112 cause the pivot arm 94 to rotate away from the integrated lancing test strip 20. This rotational movement causes the cam arm 94 to disengage from the detent mechanism 114, thereby allowing the cam arm 94 to rotate freely. When the integrated lancing test strip 20 is pulled further, the cam arm 94 continues to rotate until the blade 112 disengages from the engagement notch 39 in the lancet 30. With the integrated lancing test strip 20 disengaged from the cam arm 94, the integrated strip 20 can then be completely removed from the meter 60 for disposal or further analysis, if so desired. For subsequent tests, new integrated lancing test strips 20 can then be loaded into the meter 60 in the manner as was describe above.

From the previous discussion, it should be appreciated that the integrated lancing test strip 20 as well as the meter 60 can be used to sample and analyze body fluid from various body parts like fingers and alternate sites, such as the forearm, for example. Moreover, the integrated lancing test strip 20 can be used to analyze numerous types of body fluids, such as interstitial fluid and blood, to name a few. It also should be recognized that the features of the integrated lancing test strip 20 can be modified for use in other types of meters besides the one illustrated in the drawings. Conversely, the above-described meter 60 can be used in conjunction with other types of sampling devices, besides the above-described integrated lancing test strip 20.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. All publications, patents and patent applications cited in this specification are herein incorporated by reference as if each individual publication, patent or patent application was specifically and individually indicated to be incorporated by reference as set forth in its entirety herein.

What is claimed is:

1. An apparatus, comprising:
   a test strip adapted to analyze body fluid; and
   a packet coupled to the test strip, wherein the packet includes
      an incision forming member to form an incision in tissue,
      a guide member with a guide slot in which the incision forming member is slidably disposed, wherein the guide slot defines a guide slot opening through which the incision forming member extends during lancing, the guide member having opposing sides and an end edge located between the opposing sides, wherein the guide slot opens at the opposing sides of the guide member, wherein the guide slot opening opens at the end edge of the guide member, and
      a sterility sheet having a top layer and a bottom layer, the top layer being sealed over a top surface of the guide member, and the bottom layer being sealed over a bottom surface of the guide member to enclose the incision forming member in the guide slot, wherein the top layer and the bottom layer of the sterility sheet cover the guide slot at the opposing sides and the guide slot opening, wherein at least one of the top layer or the bottom layer of the sterility sheet seals the guide slot opening and the guide slot of the guide member to maintain sterility of the incision forming member, wherein one of the top layer or the bottom layer of the sterility sheet is positioned between the incision forming member and the test strip.

2. The apparatus of claim 1, wherein the incision forming member defines an engagement opening for engaging the incision forming member during lancing.

3. The apparatus of claim 2, further comprising:
   a meter including
      a cam arm with a blade that pierces one of the top layer or the bottom layer of the sterility sheet to engage the engagement opening of the incision forming member, and
      a firing mechanism coupled to the cam arm for firing the incision forming member.

4. The apparatus of claim 3, wherein the meter includes an adjustment mechanism to adjust position of the test strip relative to the tissue during sampling for minimizing flow constriction of the body fluid from the incision.

5. The apparatus of claim 3, wherein the test strip defines a relief opening that is aligned with the engagement opening for allowing the blade to extend completely through the engagement opening in the incision forming member.

6. The apparatus of claim 2, wherein the test strip defines a relief opening that is aligned with the engagement opening.

7. The apparatus of claim 1, wherein the test strip defines a capillary opening in which the body fluid is drawn and a notch positioned proximal the packet to direct flow of the body fluid away from the incision forming member.

8. The apparatus of claim 1, wherein:
   the incision forming member includes a lancet; and
   both the packet and test strip are flat to permit compact packaging.

9. The apparatus of claim 1, wherein the sterility sheet is hydrophobic for wiping the body fluid from the incision forming member during retraction.

10. The apparatus of claim 1, wherein the opposing sides of the guide member are flat.

11. The apparatus of claim 1, wherein the guide member has end stops inwardly extending at the guide slot opening of the guide slot.

12. The apparatus of claim 1, wherein the guide member has a body portion with one or more stop edges that are wider than the guide slot opening.

13. The apparatus of claim 12, wherein the incision forming member has a neck portion smaller than the guide slot opening extending from the body portion, wherein the neck portion is configured to be received between the one or more stop edges such that the one or more stop edges can limit rotation of the incision forming member during lancing, wherein the incision forming member has a tip extending from the neck portion configured to cut tissue.

14. The apparatus of claim 1, wherein the test strip is attached to the sterility sheet, wherein the sterility sheet is sandwiched between the test strip and the packet.

15. The apparatus of claim 1, wherein the test strip has a flat rectangular shape.

16. The apparatus of claim 1, wherein the incision forming member and the guide member are connected together via breakable tabs.

17. An apparatus, comprising:
a test strip configured to analyze body fluid;
a lancet packet attached to the test strip;
a lancet sealed inside the lancet packet to maintain sterility of the lancet, wherein the lancet packet includes a sheet having a first layer and a second layer sealed around the lancet, the first layer of the sheet is positioned between the test strip and the lancet, the lancet having an engagement opening;
a firing mechanism configured to fire the lancet, the firing mechanism having a blade piercing the lancet packet, the blade engaging the engagement opening of the lancet;
wherein the test strip defines a relief opening that is aligned with the engagement opening; and
wherein at least part of the blade of the firing mechanism extends into the relief opening of the test strip.

18. The apparatus of claim 17, further comprising:
a guide member with a guide slot in which the lancet is slidably disposed.

19. The apparatus of claim 18, wherein the guide slot has one or more end stops to retain the lancet in the lancet packet.

20. The apparatus of claim 17, wherein:
the test strip has a capillary channel opening where the body fluid enters the test strip; and
the lancet packet is located on the test strip at a position where the lancet extends proximal the capillary channel opening.

21. The apparatus of claim 17, wherein:
the test strip has a capillary channel opening;
the lancet packet has an end edge where the lancet pierces the lancet packet during lancing; and
the end edge of the lancet packet is recessed away from the capillary channel opening to promote flow of the body fluid to the capillary channel opening.

22. The apparatus of claim 17, wherein the test strip has a notch positioned proximal the lancet packet to direct flow of the body fluid away from the lancet packet.

23. The apparatus of claim 17, wherein the test strip is an electrochemical test strip.

24. The apparatus of claim 17, wherein at least a portion of the lancet packet is hydrophobic.

25. An apparatus, comprising:
a test strip adapted to analyze body fluid; and
a packet coupled to the test strip, wherein the packet includes
an incision forming member to form an incision in tissue,
a guide member with a guide slot in which the incision forming member is slidably disposed, the guide member having opposing sides and an end edge located between the opposing sides, wherein the guide slot opens at opposing sides of the guide member, wherein the guide slot defines a guide slot opening at the end edge of the guide member through which the incision forming member extends during lancing, and
a single sterility sheet having two flaps, the two flaps being sealed and wrapped around the guide member and the incision forming member to cover the incision forming member and the guide slot, wherein the two flaps of the single sterility sheet seal and cover the guide slot opening and the guide slot of the guide member to maintain sterility of the incision forming member, wherein one of the two flaps is positioned between the guide member and the test strip.

* * * * *